US008655009B2

(12) United States Patent
Chen et al.

(10) Patent No.: US 8,655,009 B2
(45) Date of Patent: Feb. 18, 2014

(54) METHOD AND APPARATUS FOR PERFORMING COLOR-BASED REACTION TESTING OF BIOLOGICAL MATERIALS

(76) Inventors: Stephen L. Chen, Anaheim, CA (US); Neeraj Kapoor, Anaheim, CA (US)

( * ) Notice: Subject to any disclaimer, the term of this patent is extended or adjusted under 35 U.S.C. 154(b) by 823 days.

(21) Appl. No.: 12/807,912

(22) Filed: Sep. 15, 2010

(65) Prior Publication Data

US 2012/0063652 A1 Mar. 15, 2012

(51) Int. Cl.
*G06K 9/00* (2006.01)
(52) U.S. Cl.
USPC .......................................... 382/100; 382/128
(58) Field of Classification Search
None
See application file for complete search history.

(56) References Cited

U.S. PATENT DOCUMENTS

| | | | | |
|---|---|---|---|---|
| 4,843,377 | A | * | 6/1989 | Fuller et al. ............... 340/573.4 |
| 4,976,923 | A | | 12/1990 | Lipsky et al. |
| 5,119,830 | A | | 6/1992 | Davis |
| 5,260,219 | A | * | 11/1993 | Fritz .............................. 436/71 |
| 5,360,013 | A | * | 11/1994 | Gilbert ......................... 600/584 |
| 5,408,535 | A | * | 4/1995 | Howard et al. ............... 382/128 |
| 5,470,750 | A | * | 11/1995 | Bar-Or ........................... 436/63 |
| 5,501,837 | A | | 3/1996 | Sayles |
| 5,595,187 | A | | 1/1997 | Davis |
| 5,976,469 | A | | 11/1999 | Davis |
| 6,514,461 | B1 | | 2/2003 | Lappe et al. |
| 6,565,814 | B1 | | 5/2003 | Anraku et al. |
| 7,267,799 | B1 | | 9/2007 | Borich et al. |
| 7,292,718 | B2 | | 11/2007 | Douglass |
| 7,313,257 | B2 | * | 12/2007 | Roman ......................... 382/128 |
| 7,420,663 | B2 | | 9/2008 | Wang et al. |
| 7,652,268 | B2 | * | 1/2010 | Patel ........................... 250/484.5 |
| 8,150,115 | B2 | * | 4/2012 | Capewell ..................... 382/128 |
| 2003/0108450 | A1 | | 6/2003 | Mainquist et al. |
| 2005/0221504 | A1 | | 10/2005 | Petruno et al. |
| 2007/0026530 | A1 | | 2/2007 | Wu et al. |
| 2008/0287316 | A1 | | 11/2008 | Spivey et al. |

OTHER PUBLICATIONS

International Search Report and Written Opinion dated Dec. 30, 2011 (Eleven (11) pages).
International Search Report and Written Opinion dated May 21, 2012 (Seven (7) pages).

* cited by examiner

*Primary Examiner* — Manav Seth
(74) *Attorney, Agent, or Firm* — Crowell & Moring LLP (57) ABSTRACT

Color-based reaction testing of biological materials may be performed by capturing, in an uncalibrated environment, a digital image of an exposed test strip, together with an adjacently-located reference color chart or on-strip color chart. The image data specifically representing the individual test pads on the test strip, as well as the reference color blocks on the reference chart, are then located within the captured image, and compared to identify any color matches between the test pads and the corresponding sequences of reference color block. Based on this comparison operation, a set of test results can be generated which effectively identifies which of the reference chart's color blocks most closely matches the color of the corresponding dipstick's test pads. The generated test results may then be provided to the user in a printed or displayed form. Alternatively, the test results may simply be stored for later retrieval.

20 Claims, 10 Drawing Sheets
(6 of 10 Drawing Sheet(s) Filed in Color)

FIG. 1A

PRIOR ART

METHOD AND APPARATUS FOR PERFORMING COLOR-BASED REACTION TESTING OF BIOLOGICAL MATERIALS

FIELD OF THE INVENTION

The present invention relates generally to analyzing biological materials (e.g., urine, blood, saliva, feces, sweat and other biological materials) and more particularly to an improved method and electronic user device for performing color-based reaction testing of such biological materials in an accurate and precise, yet cost effective manner.

BACKGROUND OF THE INVENTION

Testing of biological materials may include the use of color-based reaction testing, whereby a test pad is exposed to urine, blood, saliva, feces or sweat. For example, urinalysis is an array of tests performed on urine and one of the most common methods of medical diagnosis. Urinalysis is used as a screening and/or diagnostic tool by virtue of being able to detect substances or cellular material in the urine associated with different metabolic and kidney disorders. For example, substances such as protein or glucose will begin to appear in the urine before patients are aware that they may have a problem.

Figure 1A:
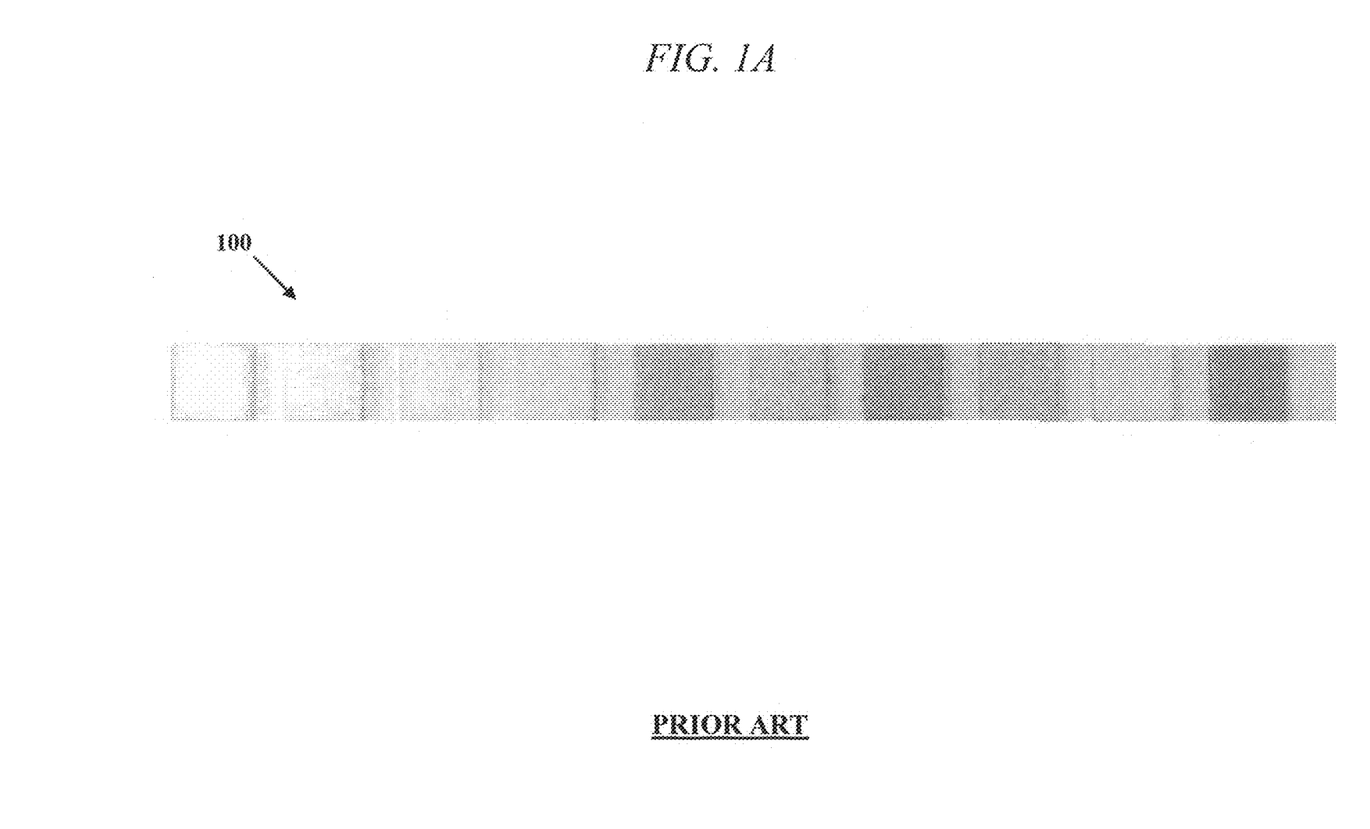
FIG. 1A depicts a typical urinalysis test strip or dipstick.

Color-based reaction testing, such as urinalysis, is typically performed using "dipsticks," which are strips of plastic or sturdy paper to which a series of reagent test pads have been affixed, as shown in FIG. 1A. Each reagent test pad on the dipstick 100 is chemically treated with a compound that is known to change color in the presence of particular reactants. For example, in the context of urinalysis, the dipstick 100 will typically include reagent pads for detecting or measuring glucose, bilirubin, ketone (acetoacetic acid), specific gravity, blood, pH, protein, urobilinogen, nitrite and leukocytes in urine.

The process of testing biological materials involves first submerging or otherwise exposing the aforementioned dipsticks and affixed reagent pads to a subject's urine, saliva, blood, feces, sweat. If the urine contains quantities of the particular reactants, one or more of the reagent test pads will change color as a result. The magnitude of the change is further indicative of the amount of the particular reactants that are present.

Figure 1B:
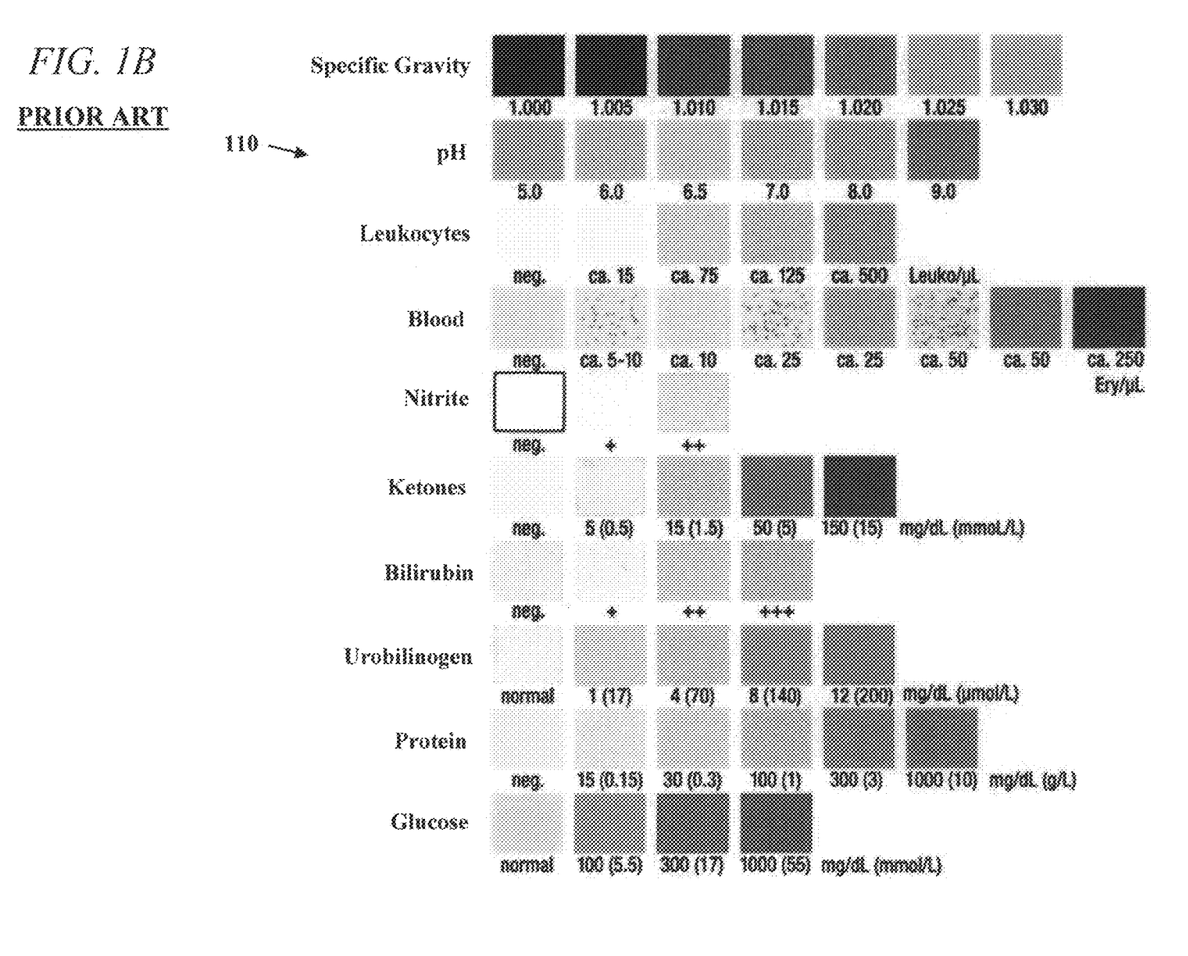
FIG. 1B depicts a typical reference color chart for use in urinalysis.

Urinalysis dipsticks, for example, are typically accompanied with a reference color chart, such as chart 110 shown in FIG. 1B, for evaluating test pad color changes following exposure to urine. As shown in FIG. 1B, the typical reference color chart 110 will include a spectrum of possible colors associated with each corresponding reagent pad on the dipstick, thereby allowing a healthcare provider to "read" the test results with the naked eye. However, manually comparing different shades of a given color can be difficult to perform and lead to unacceptably lower accuracy. Thus, it is preferable for healthcare providers to use a specialized electronic reader to eliminate the subjectivity of visual color interpretation, thereby making the color-based reaction testing process simpler and more reliable. Such electronic readers are highly-calibrated devices that typically use either reflectance photometers or charge coupled device (CCD) image sensors. Specifically, since the process of accurately capturing and comparing color is so vital to the process, the image-capturing environment has to be precisely controlled across different tests since even slight variations in ambient light, test pad location or image-capturing angle can lead to inaccurate results. Moreover, there is even substantial variation across different CCD sensors meaning that each reader has to be individually calibrated.

The problem is that such electronic readers are typically too expensive for most smaller laboratories to use. Moreover, since these readers have to be so highly calibrated, they are closed, non-mobile devices, meaning that the resulting test data is not readily portable and that the actual test has to be performed wherever the electronic reader happens to be located.

Accordingly, there is a need to provide an alternative approach to reading color-based reaction test results of such biological materials that is more accurate and precise than manual reading, yet also cost effective.

SUMMARY OF THE INVENTION

Disclosed and claimed herein is a method and electronic user device for performing color-based reaction testing of such biological materials. In one embodiment, the method includes capturing digital image information of an exposed test strip and a reference color chart in an uncalibrated environment. The exposed test strip includes a plurality of test pads and the reference color chart includes a plurality of color blocks arranged in a plurality of test-specific sequences. The method further includes locating first image data within the digital image information corresponding to each of the plurality of test pads, and locating second image data within the digital image information corresponding to each of the plurality of color blocks on the reference color chart. Both the first and second image data includes color information.

Thereafter, the method includes matching color information from the first image data to corresponding color information from the second image data, and then generating test results based on that matching operation.

Other aspects, features, and techniques of the invention will be apparent to one skilled in the relevant art in view of the following description of the exemplary embodiments of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The features, objects, and advantages of the present invention will become more apparent from the detailed description set forth below when taken in conjunction with the drawings in which like reference characters identify correspondingly throughout, and wherein.

DETAILED DESCRIPTION OF THE EXEMPLARY EMBODIMENTS

Overview of the Disclosure

The present disclosure relates generally to performing color-based reaction testing of biological materials in an uncalibrated environment. In one embodiment, a digital image of a biological material test strip (e.g., urine test strip), together with an adjacently-located reference color chart, may be captured by an electronic user device in an uncalibrated environment.

Once the image data has been captured, the image data specifically representing the individual test pads on the test strip, as well as the reference color blocks on the reference chart, are then located within the captured image, such as by using an image processing algorithm executing on the electronic user device. Thereafter, the diagnostic client may compare the color data associated with each of the previously-located test pads with the corresponding color data for the reference color blocks. Since each test pad will have an associated test-specific sequence of color blocks on the reference chart organized in either a row or column, the color information for a given test pad need only be compared with its corresponding test-specific sequence of color blocks on the reference chart.

The above comparison operation may be performed to identify any color matches between the test pads and the corresponding sequences of reference color block. In certain embodiment, this color matching operation may be performed using a Lab color space analysis.

In any event, based on this comparison operation, a set of test results can be generated which effectively identifies which of the reference chart's color blocks most closely matches the color of the corresponding dipstick's test pads. Since each of the reference color blocks are associated with a particular test result (e.g., negative, positive, very positive, etc.), the actual test result corresponding to the matching color block may be readily determined, e.g., using a lookup table that correlates particular color blocks with corresponding test results. The generated test results may then be provided to the user in a printed or displayed form. Alternatively, the test results may simply be stored for later retrieval.

In this fashion, the novel methodology of the invention enables color-based reaction testing of such biological materials to be performed in an uncalibrated environment, unlike the highly-calibrating conditions required by prior art systems. This advancement in the technological arts is made possible, at least in part, based on the fact that the color data associated with the reference color chart and the color data associated with the exposed test strip are equally impacted by the specific camera used and the specific ambient lighting conditions under which the data was collected. Therefore, the color data of the test strip is automatically normalized against the reference to which it needs to be compared (i.e., the reference chart), thereby rendering calibration unnecessary. This, in turn, enables virtually any user device, whether general- or special-purpose, that is equipped with a camera to be used in performing what was previously only possible using expensive and highly calibrated equipment. This would allow for mobile and even remote testing of biological materials (for example in rural villages and such) to be performed at both a low cost and with a higher accuracy and precision than manual inspection.

As used herein, the terms "a" or "an" shall mean one or more than one. The term "plurality" shall mean two or more than two. The term "another" is defined as a second or more. The terms "including" and/or "having" are open ended (e.g., comprising). Reference throughout this document to "one embodiment", "certain embodiments", "an embodiment" or similar term means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner on one or more embodiments without limitation. The term "or" as used herein is to be interpreted as inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

In accordance with the practices of persons skilled in the art of computer programming, the invention is described below with reference to operations that are performed by a computer system or a like electronic system. Such operations are sometimes referred to as being computer-executed. It will be appreciated that operations that are symbolically represented include the manipulation by a processor, such as a central processing unit, of electrical signals representing data bits and the maintenance of data bits at memory locations, such as in system memory, as well as other processing of signals. The memory locations where data bits are maintained are physical locations that have particular electrical, magnetic, optical, or organic properties corresponding to the data bits.

When implemented in software, the elements of the invention are essentially the processor-executable code segments to perform the necessary tasks. The code segments can be stored in a "processor executable storage medium," which includes any medium that can store information. Examples of the processor executable storage mediums include an electronic circuit, a semiconductor memory device, a ROM, a flash memory or other non-volatile memory, a floppy diskette, a CD-ROM, an optical disk, a hard disk, etc.

Finally, when a test pad is described herein as being an "exposed" test pad, it means that the test pad has been in contact with, or otherwise exposed to either urine, blood, saliva, feces, sweat or any other biological materials.

Overview of an Exemplary Embodiments

Figure 2A:
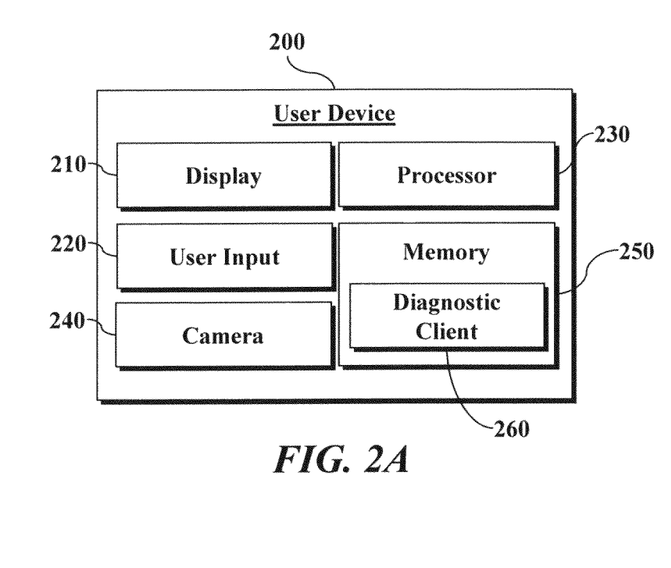
FIGS. 2A-2B depict one or more embodiments of an electronic user device configured to implement one or more aspects of the invention.
Figure 2B:
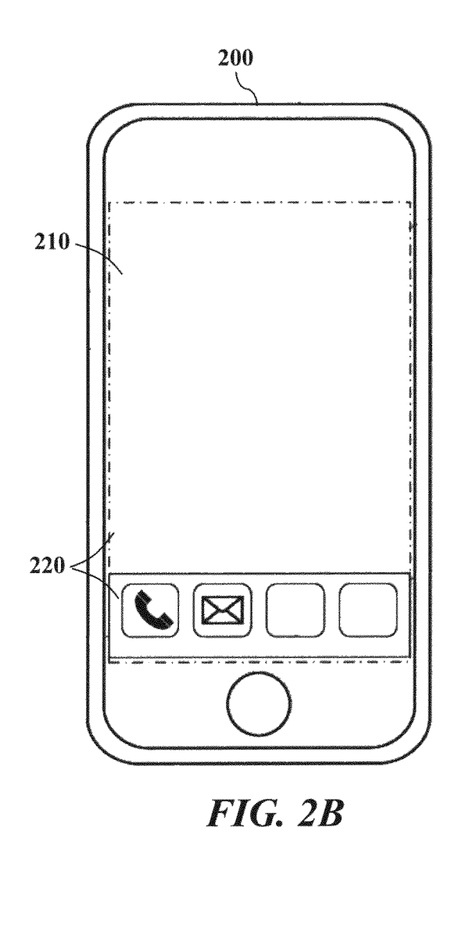

FIGS. 2A-2B depict one or more embodiments of a user device 200 configured to implement one or more aspect of the invention. The user device 200 may be any electronic user device, such as a cellular telephone, smartphone, personal digital assistant (PDA), handheld computer, etc. As such, and as shown in FIG. 2A, the user device 200 may include a display 210, such as a liquid crystal display or any other known type of display usable in connection with such an electronic user device. The user device 200 may also include a user input 220, which may include one or more buttons or keys in the form of a keypad, number pad, keyboard or any other collection of individual keys, buttons or the like. In another embodiment, the user input 220 may be integrated with the display 210 in the form of a touchscreen.

The user device 200 preferably also includes a processor 230 and a camera 240. The camera 240 may be based on CCD technology or Complementary metal-oxide-semiconductor (CMOS) image sensor technology, such as would be the case with the cameras typically equipped on modern day smartphones. Similarly, however, the camera 240 may be based on other known types of image-capturing technology.

Finally, the user device 200 is shown as having memory 250 which, among other programs, software modules, data and operating system files, stores a diagnostic software client 260. When the client 260 is loaded from memory 250 and executed by processor 230, it performs one or more aspects of the invention, as more fully detailed below with respect to FIGS. 3A-3B.

FIG. 2B depicts another illustration of the user device 200 having a particular configuration in which display 210 functions as both a display screen, as well as a portion of the user input 220 by virtue of being a touchscreen.

Figure 3A:
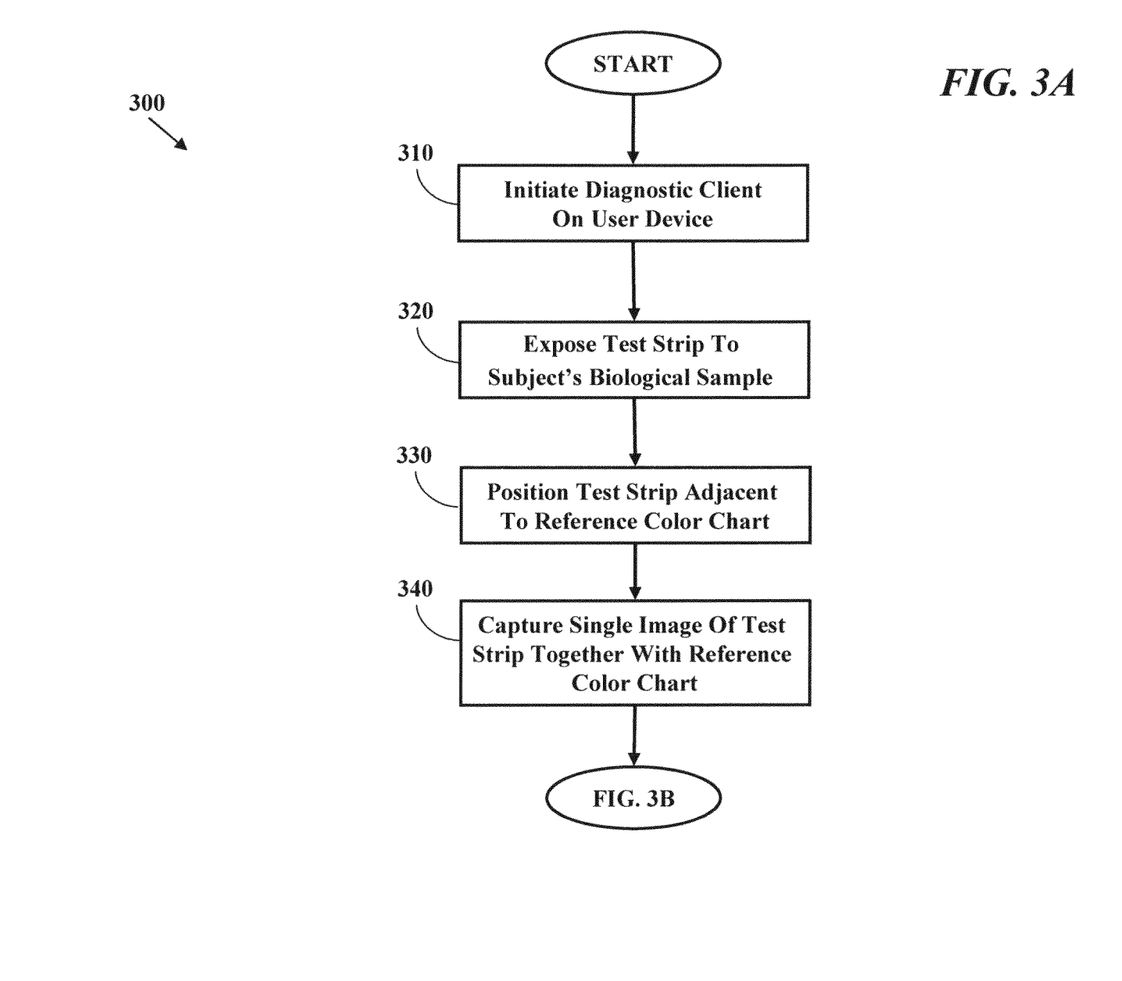
FIGS. 3A-3B depict one embodiment of a process for performing one or more aspects of the invention.
Figure 3B:
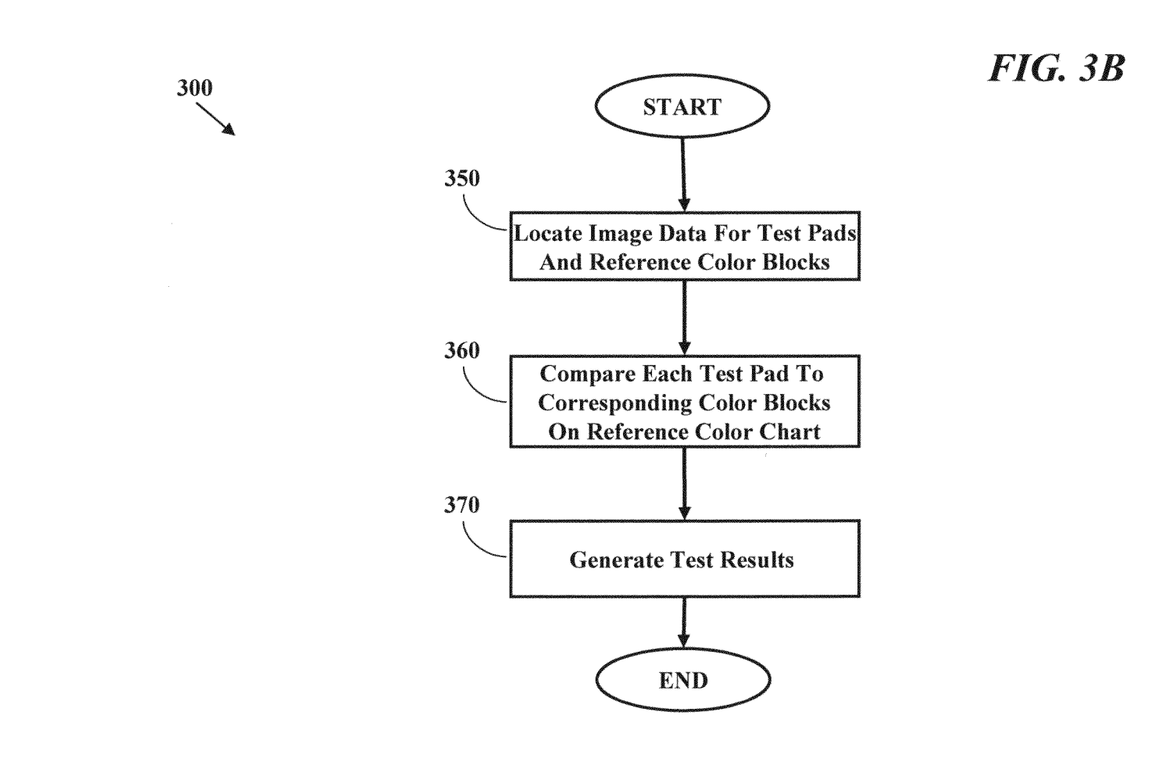

Referring now to FIGS. 3A-3B, depicted is one embodiment of a process 300 for carrying out one or more aspects of the invention. In certain embodiments, process 300 may be performed by a mobile user device, such as user device 200, although in other embodiments the user device may be any electronic device configured and programmed to perform the computer-implemented operations of process 300. While process 300 may be applied in the context of urinalysis, it should equally be appreciated that process 300 may be carried in the contexts of testing other biological materials as well, such as blood, saliva, feces and sweat.

In any event, however, as shown in FIG. 3A process 300 begins at block 310 with the diagnostic client (e.g., client 260) being initiated on the user device. Thereafter, at block 320.*a* test strip or dipstick would be exposed to a subject's biological sample (e.g., urine), as would typically be the case. The exposed test strip would then be positioned adjacent to a reference color chart, such as on a flat horizontal or vertical surface (block 330). Process 300 may then continue to block 340 where a single image of the test strip, together with the adjacently-located reference color chart, may be captured by the user device. It should be appreciated that the user device may be preferably equipped with a CCD or CMOS camera (e.g., camera 240) for use in capturing the image at block 340. In an alternative embodiment, the test strip and reference color chart may be photographed at different times rather than as a single image, so long as the ambient photographing conditions are essentially the same.

Moreover, it is preferably the case that the image capturing operation of FIG. 3A be performed in an uncalibrated environment, as would have been necessary with prior art systems requiring highly-calibrating conditions. As previously described, this advancement in the technological arts is made possible since the color data associated with the reference color chart and the color data associated with the exposed test strip are equally impacted by the specific camera used and the specific ambient lighting conditions under which the data was collected. Therefore, the color data of the test strip is automatically normalized against the reference to which it needs to be compared (i.e., the reference chart), thereby rendering calibration unnecessary.

Once the image data has been captured, process 300 continues to block 350 of FIG. 3B where the captured image data may be processed. Namely, the image data specifically representing the individual test pads on the exposed test strip, as well as the reference color blocks on the reference chart, must be first located within the captured image by an image processing algorithm of the diagnostic client (block 350). As will be described in more detail below with references to FIGS. 4A-4C, this may be done using a template matching operation in which the captured image data may be compared against a reference in order to identify common patterns or features. Alternatively, a 'shape location' algorithm, such as the 'square algorithm' included in the OpenCV (Open Source Computer Vision) software package, may be used. In general terms, such 'shape location' or similar algorithms are based on analyzing image data for the occurrence of distinct edges or transitions as a way to identify the position of specific features of interest. It should be appreciated, however, that other known image processing means may be similarly used to locate the image data representing the individual test pads on the exposed test strip, as well as the reference color blocks on the reference chart.

Once the operation of block 350 has been completed, process 300 may then continue to block 360 where an image data comparison operation is carried out. In particular, the diagnostic client compares the color data associated with each of the previously-located test pads with the similarly-located color data for the reference color blocks. For example, and as will be described in more detail below with reference to FIGS. 4A-4C, each test pad will have an associated test-specific sequence of color blocks on the reference chart organized in either a row or column. This test-specific sequence of color blocks includes all of the possible different colors that the reagent on the test pad is chemically capable of producing when exposed to reactants. Therefore, a given test pad need only be compared with this corresponding test-specific sequence of color blocks.

The goal of this comparison operation is to identify color matches between the test pads and the corresponding sequences of reference color block. This color matching operation comprises performing a color space analysis on image data—the particularly-identified image data from block 350 above. Although the RGB color space is typically what would be used in such computer-implemented systems, another aspect of the invention is to rather use the Lab color space for performing the comparison or matching operation of block 360. In the RGB color space, each pixel has a 'red' component, a 'green' component, and a 'blue' component which, when mixed together, produces the colors we see on a computer screen. In contrast, however, the Lab color space is a color-opponent space with dimension L for lightness, and dimensions a and b for the color-opponent dimensions.

Due to differences between the way computers analyze color data and the way the human eye processes colors, there are some circumstances in which computers may interpret the RGB color space differently than one would expect. In the context of color-based reaction testing, in particular, the inventor has found that using the Lab color space rather than the RGB color space produces more accurate results.

Based on the comparison operation of block 360, process 300 will generate a set of test results at block 370. That is, the comparison operation of block 360 will effectively identify which of the reference chart's color blocks most closely matches the color of the corresponding dipstick's test pads. Since each of the reference color blocks are associated with a particular test result (e.g., negative, positive, very positive, etc.), as shown for example in FIG. 1B, the test result corresponding to the matching color block may be easily generated (block 370). By way of a non-limiting example, a lookup table stored in memory (e.g., memory 250) that correlates particular color blocks with corresponding test results may be used. Thereafter, process 300 ends.

Additionally, however, once generated the test results may be provided to the user, and it should further be appreciated that such test results may be provided in any form, including printed or displayed. Alternatively, the test results may simply be stored for later retrieval.

In this fashion, the novel methodology of the invention enables color-based reaction testing of biological materials to be performed in an uncalibrated environment. This enables virtually any user device, whether general- or special-purpose, that is equipped with a camera to be used in performing what was previously only possible using expensive and highly calibrated equipment. This would allow for mobile and even remote testing of biological materials (for example in rural villages and such) to be performed at both a low cost and with higher levels of accuracy and precision than manual inspection.

It should further be appreciated that the uncalibrated image capturing operation of block 340 above may be performed in any number of ways or environments. For example, in certain embodiments a casing may be used, inside which the reference color chart has been affixed. The casing may further include a first opening for inserting test strips into a position that is adjacent or near the affixed chart. The combined image of block 340 may then be captured through a second opening in the casing that is located opposite to the side of the reference chart and inserted test strip.

Rather than a casing, any relatively flat surface (horizontal or vertical) may be used which allows the reference chart and test strip to be photographed under essentially the same ambient conditions.

Figure 4A:
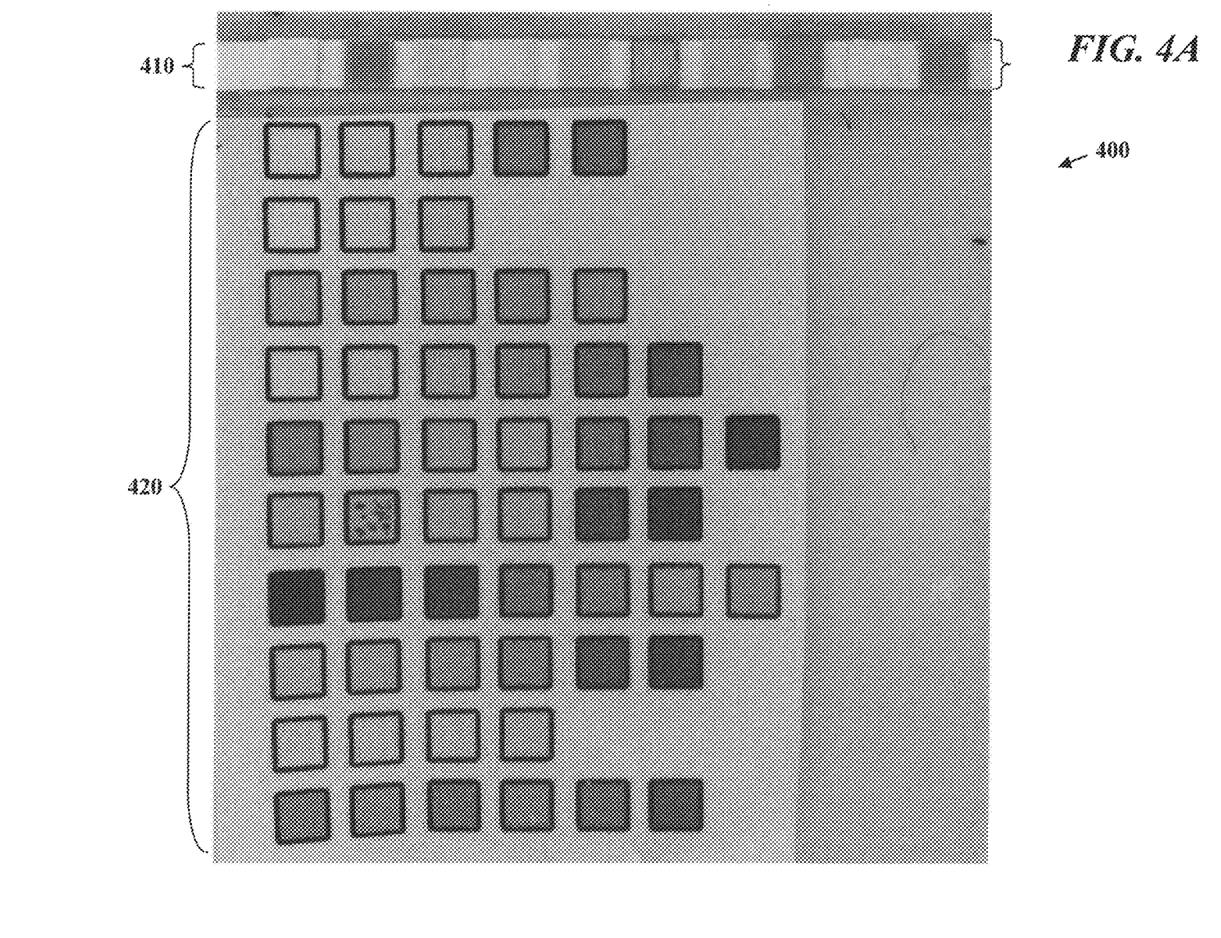
FIGS. 4A-4C depict images taken by a user device (e.g., user device of FIGS. 2A-2B) usable in connection with the principles of the invention.

Referring now to FIG. 4A, depicted is a one embodiment of a captured image 400, such as the captured image described above with reference to block 340 of FIG. 3A. As shown in FIG. 4A, the exposed test strip 410 was positioned near the color reference chart 420, and the combination of the two photographed together by a user device equipped with a camera (e.g., user device 200).

Figure 4B:
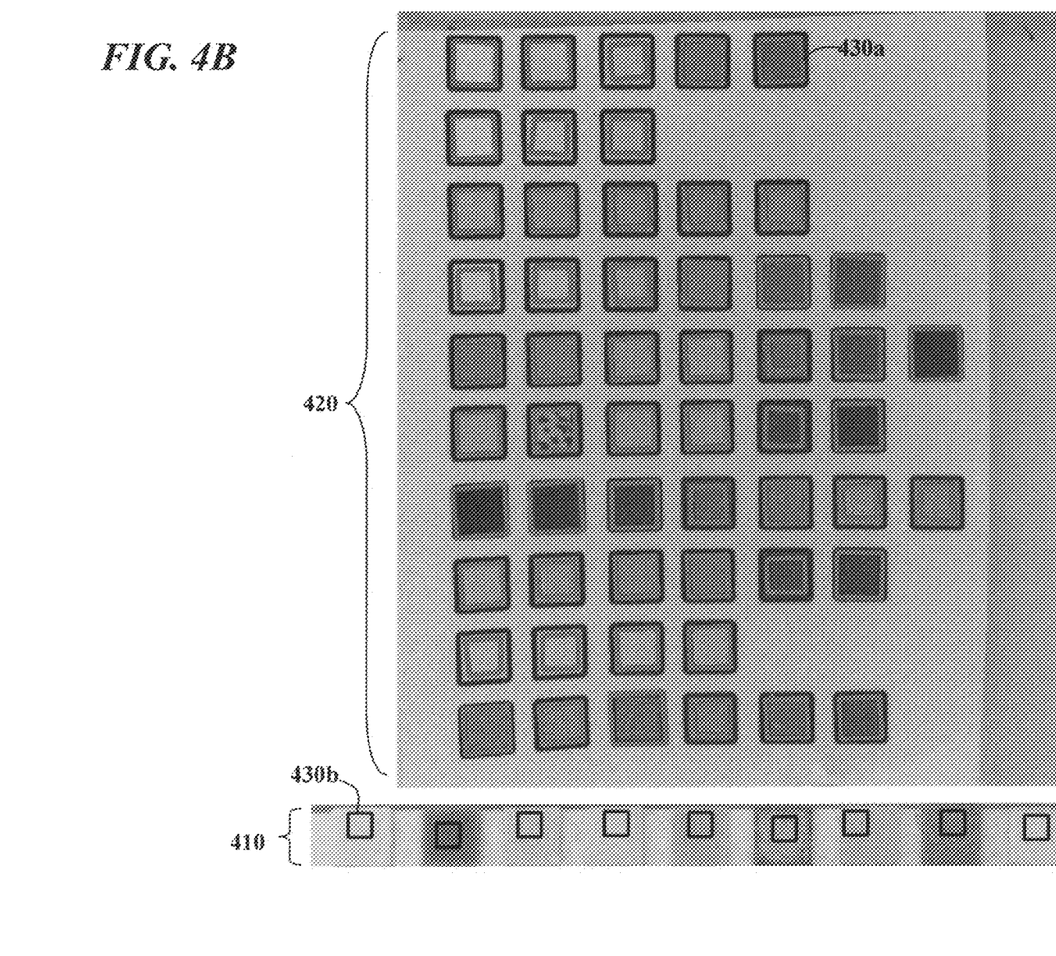

FIG. 4B depicts one embodiment of how the captured image 400 may then be processed to locate the image data corresponding to the individual test pads and reference color blocks, as described above with reference to block 350 of FIG. 3A. In particular, and as shown in FIG. 4B, a shape location algorithm (see e.g., OpenCV) has been applied to the color reference chart 420. A black border has been added to each of the reference color blocks in order to enhance the algorithm's ability to detect the edges of the individual color backs of chart 420. The successful identification of a color block is reflected in each case by a 'square marker,' such as green square marker 430a shown in FIG. 4B. While this identification data may be displayed to the user so that the user can verify that the reference color blocks have been properly identified, in other embodiments this operation may be a background process.

Referring to the test strip 410 now, rather than using a shape location algorithm, the individual test pads are located using a template matching operation in which the captured image data corresponding to the test strip 410 is directly compared against a reference image of a test strip. With template matching, each pad is located based, at least in part, on matching the captured image data of the test strip 410 to a known pattern of a test strip and to interpolate the location of individual test pads based on expected position.

Once located, a representative area on each of the test pads may be identified. For example, as shown in FIG. 4B, the color image data contained within the area defined by square 430b may be used as the image data corresponding to the first pad of test strip 410. Similarly, areas within each of the subsequent test pads may be defined and used in the color matching operation to follow (e.g., comparison operation of block 360 of FIG. 3B).

While FIG. 4B was described as having used template matching to locate the test pads on test strip 410 and a shape location algorithm for locating the color blocks of reference chart 420, it should equally be appreciated that either technique may be used in either case. Similarly, other known image processing means may also be used.

Once the locations of the individual test pads on the test strip 410 have been located using either template matching, a shape location algorithm, etc., it may be preferable to average the color data within the defined area (e.g., square 430b) so as to account for minor color variations from point-to-point. While the color blocks of the reference chart may similarly be averaged, it is less likely that there will be significant color variation within the reference color blocks.

Figure 4C:
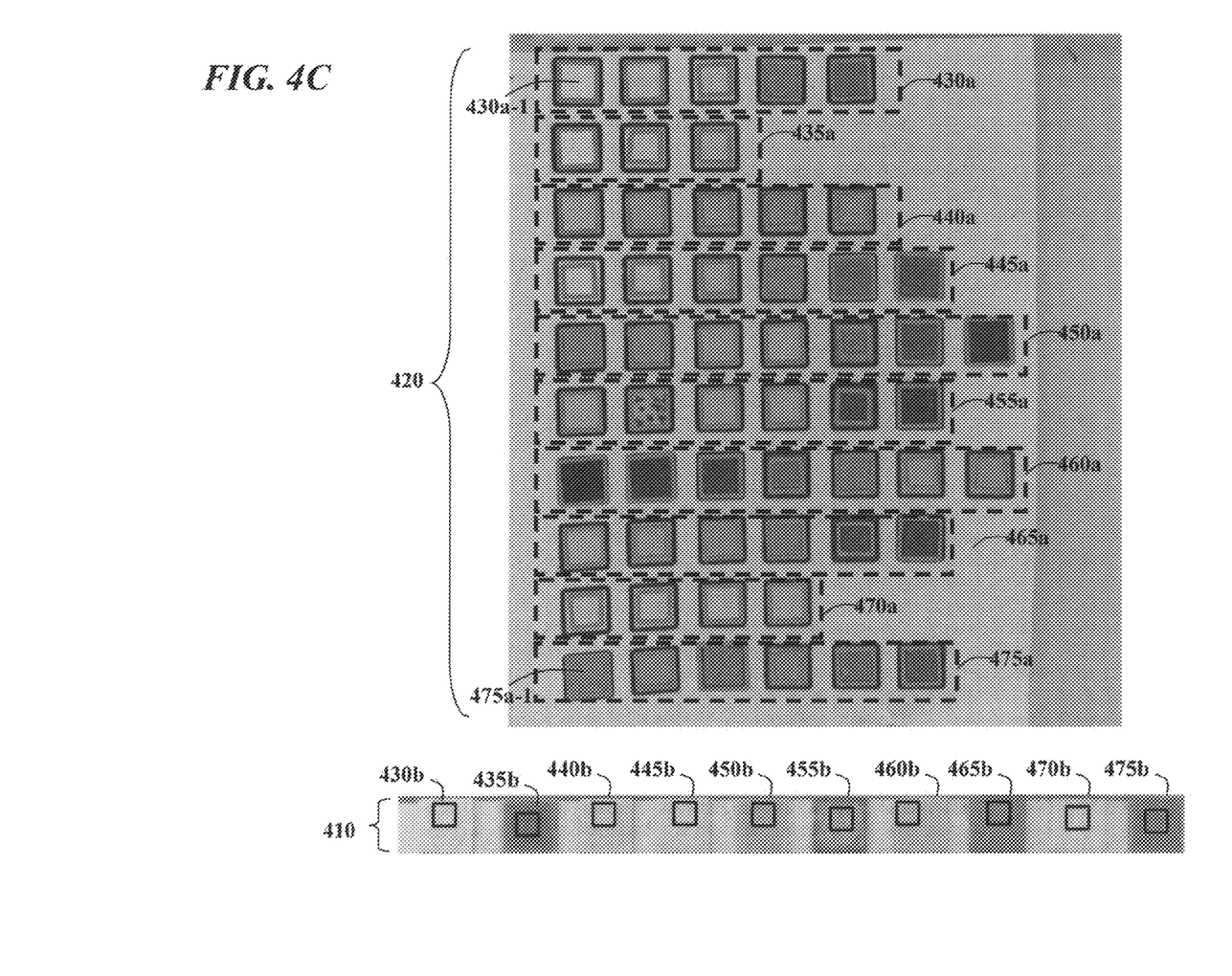

Referring now to FIG. 4C, depicted is one embodiment of how the comparison operation, as described above with reference to block 360 of FIG. 3B, may be performed. In particular, the color blocks of color reference chart 420 are shown as being grouped into separate color block sequences 430a-475a. Correspondingly, the image data for each of the individual test pads of the test strip 410 have been identified as test pad areas 430b-475b. As previously described, each test pad need only be compared with the corresponding color blocks that it is capable of matching. Moreover, since the reference chart 420 is organized into individual rows, where each row corresponds to the detection of a particular substance or cellular material, each test pad area (430b-475b) need only be compared with its corresponding color block sequence 430a-475a. For example, the color data of test pad area 430b would only be compared with each of the color blocks in sequence 430a, the test pad area 435b would only be compared with each of the color blocks in sequence 435a, and so forth.

As initially described above with reference to block 360, this comparison operation will result in identifying, for each test pad area (430b-475b), which of the reference chart's color blocks most closely matches. Then, lookup operation may be performed to identify the particular test result (e.g., negative, positive, very positive, etc.) that corresponds to that particular reference color block. For example, in the case of test pad area 430b, the closest match was determined to be color block 430a-1. The known test results that correspond to that color block would then be found in a table, stored in memory, etc. (See e.g., FIG. 1B). Additionally, and by way of example only, for test pad area 475b the closest match was determined to be color block 475a-1. Again, the test results (e.g., negative, positive, very positive, etc.) that correspond to color block 475a-1 could then be looked up.

Figure 5:
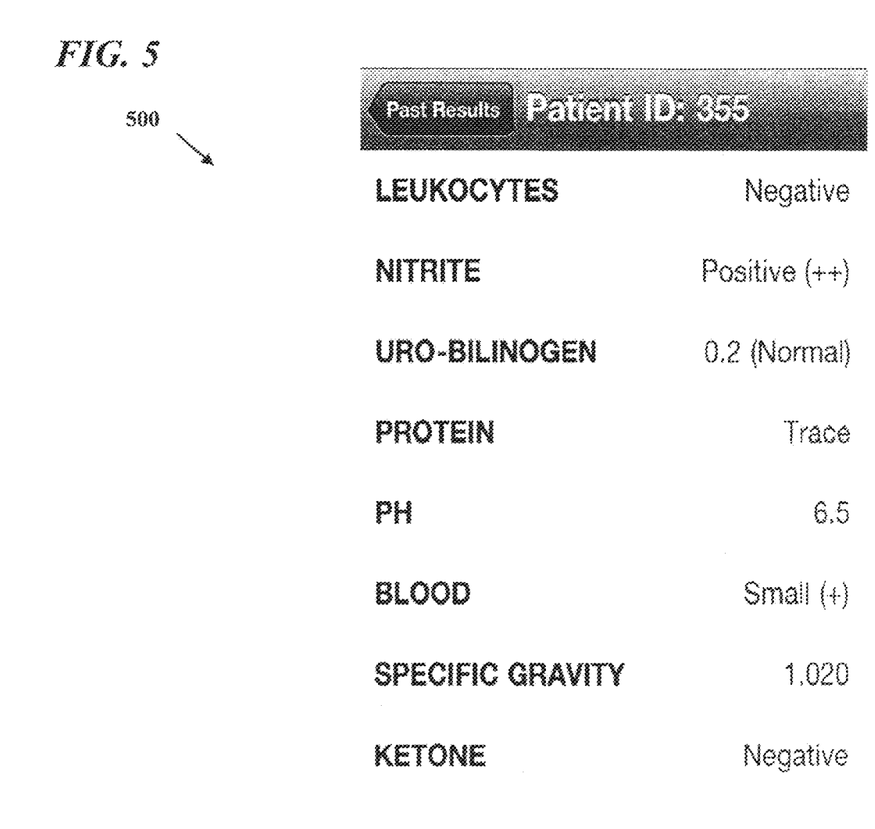
FIG. 5 depicts a screenshot from a user device (e.g., user device of FIGS. 2A-2B) showing various test results generated in accordance with the principles of the invention.

Once the test result data has been obtained for each of the test pads, the results may be reported to the user in any number of formats. FIG. 5, for example, depicts one embodiment of a screenshot 500 that may be displayed to a user on a user device screen (e.g., display 210) summarizing the results of the test associated with each of the test pads.

Rather than capturing a combined image with both the exposed test strip, as well as the reference color chart, photographs of a series of reference color charts may be captured under varying ambient conditions as an alternative way of implementing the invention. Such images may be stored for later comparison to exposed test strips.

By way of example, after an image of an exposed test strip has been captured, the ambient conditions under which that exposed test strip was captured may be determined and then compared to the varying ambient conditions under which the previously-stored reference color charts were captured. The stored reference chart that was taken under conditions most closely approximating those under which the exposed test strip was taken would then be used for the image data comparison operation of block 360, as described above.

Figure 6:
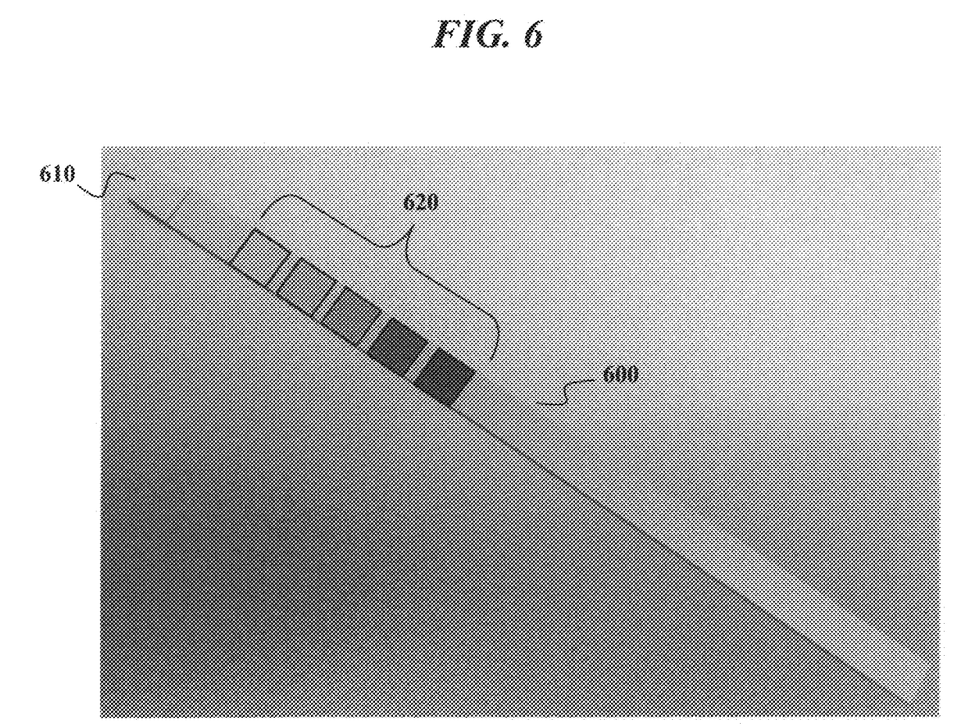
FIG. 6 depicts an embodiment of a test strip capable of implementing one or more aspects of the invention.

Referring now to FIG. 6, the aforementioned reference color chart may be incorporated into the test strip itself. In particular, test strip 600 is shown as having both a test pad 610 and a reference color sequence 620. With this embodiment, process 300 (as described above with reference to FIGS. 3A-3B) could be performed with the only modification being that block 330 would not be needed. Thus, all of the disclosure above relating to process 300 may be similarly performed using test strip 600.

Additionally, a captured image of test strip 600 may then be processed in the same manner as captured image 400, as described above with reference to FIGS. 4A-4C. Namely, an image of test strip 600, after being exposed, may be processed to locate the image data corresponding to the individual test pad 610 and the reference color sequence 620 using either the aforementioned shape location algorithm or template matching operation.

Once located, a representative area on test pad 610 may be identified, as was shown above in FIG. 4B. The color data of this representative area may also be averaged so as to account for minor color variations from point-to-point. Thereafter, the comparison operation described with respect to block 360 of FIG. 3B and shown in FIG. 4C may similarly be performed on the test strip 600. Obviously, however, in the embodiment of FIG. 6 it would not be necessary to identify which sequence to compare the test strip color data to since there is only a single sequence. However, while only a single test pad 610 and corresponding reference color sequence 620 is shown in FIG. 6, the improved test strip 600 may similarly contain additional test pads and corresponding reference sequences.

It should be appreciated, however, that other known image processing means may be similarly used to mark the image data representing the individual test pads on the exposed test strip, as well as the reference color blocks on the reference chart. In addition, identifying marks (e.g., barcodes) may be used on the test strip itself to insure that only certified test strips may be used with this system, thereby effectively creating a 'closed system.' In such an embodiment, only properly marked test strips may be recognized or processed by the software (e.g., diagnostic software client 260).

In one or more additional embodiments, instead of individual reference color blocks, a continuous color spectrum may be used so as to provide more precise test results. This may be particularly advantageous in the context of the embodiment shown in FIG. 6, wherein the color reference sequence 620 would be a continuous color spectrum rather than individual, discretized colors.

It should further be appreciated that since all of the biological material test results are automatically captured by the user device itself, such data can be easily exported and/or manipulated. For example, it would be possible to e-mail test results directly to patients or other healthcare providers. Similarly, results may be uploaded directly to an online health information system, a laboratory information system, or the like. Moreover, test results may be graphed over time so as be able to track patient health.

The ease of use, portability and calibration-independent nature of the invention allows color-based reaction testing of biological materials, such as urine, to be performed even by the patients at home.

The principles of the invention may be further applied to pregnancy tests by performing image analysis on the pregnancy test to confirm the presence of lines, i.e., indicate positive or negative presence of hCG). In the context of saliva testing, the principles of the invention may be extended to include alcohol consumption testing since saliva can be used to detect the presence and, to some extent, the quantity of alcohol present in a subject's saliva.

In one or more additional embodiments of the invention, principles of the invention may be extended to perform urine sedimentation analysis and even certain blood test by attaching or integrating a microscope lens to the camera of the user device. The resulting image data may be similarly analyzed using the methodologies disclosed herein.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art. Trademarks and copyrights referred to herein are the property of their respective owners.

What is claimed is:

1. A method for color-based reaction testing of biological materials comprising the acts of:
    capturing digital image information of an exposed test strip and a reference color chart in an uncalibrated environment, wherein the exposed test strip comprises a plurality of test pads, and wherein further the reference color chart comprises a plurality of color blocks arranged in a plurality of test-specific sequences;
    locating first image data within the digital image information corresponding to each of the plurality of test pads, said first image data having color information;
    locating second image data within the digital image information corresponding to each of the plurality of color blocks on the reference color chart, said second image data having color information;
    matching color information from the first image data to corresponding color information from the second image data; and
    generating test results based on said matching.

2. The method of claim 1, wherein capturing the digital image information comprises capturing both the exposed test strip and the reference color chart as a single digital image in the uncalibrated environment.

3. The method of claim 1, wherein locating first image data comprises applying one of a shape location algorithm and a template matching operation to the first image data.

4. The method of claim 1, wherein locating second image data comprises performing applying one of a shape location algorithm and a template matching operation to the second image data.

5. The method of claim 1, further comprising averaging color information across the first image data, and wherein matching the color information comprises matching the averaged color information for the first image data to corresponding color information from the second image data.

6. The method of claim 1, wherein matching comprises matching color information corresponding to a first test pad of the plurality of test pads to color information corresponding to a first test-specific sequence of the plurality of test-specific sequences.

7. The method of claim 6, wherein matching further comprises matching color information corresponding to a second test pad of the plurality of test pads to color information corresponding to a second test-specific sequence of the plurality of test-specific sequences.

8. The method of claim 1, wherein matching further comprises matching color information from the first image data to corresponding color information from the second image data by performing Lab color space analysis on the color information from the first and second image data.

9. The method of claim 1, wherein capturing the digital image information comprising capturing the digital image information by a mobile user device, and wherein the method further comprises displaying the test results on a display of the mobile user device.

10. A mobile electronic device comprising:
- a memory containing processor-executable instructions, including a diagnostic client for performing color-based reaction testing of biological materials; and
- a processor electrically coupled to the memory, the processor configured to execute the diagnostic client to:
  - capture digital image information of an exposed test strip and a reference color chart in an uncalibrated environment, wherein the exposed test strip comprises a plurality of test pads, and wherein further the reference color chart comprises a plurality of color blocks arranged in a plurality of test-specific sequences,
  - locate first image data within the digital image information corresponding to each of the plurality of test pads, said first image data having color information,
  - locate second image data within the digital image information corresponding to each of the plurality of color blocks on the reference color chart, said second image data having color information,
  - match color information from the first image data to corresponding color information from the second image data, and
  - generate test results based on said matching.

11. The mobile electronic device of claim 10, wherein the processor is further configured to capture the digital image information by capturing both the exposed test strip and the reference color chart as a single digital image in the uncalibrated environment.

12. The mobile electronic device of claim 10, wherein the processor is further configured to locate first image data by applying one of a shape location algorithm and a template matching operation to the first image data.

13. The mobile electronic device of claim 10, wherein the processor is further configured to locate second image data by applying one of a shape location algorithm and a template matching operation to the second image data.

14. The mobile electronic device of claim 10, wherein the processor is further configured to execute the diagnostic client to average color information across the first image data, and wherein the processor matches said color information by matching the averaged color information for the first image data to corresponding color information from the second image data.

15. The mobile electronic device of claim 10, wherein the processor is further configured to match color information by matching color information corresponding to a first test pad of the plurality of test pads to color information corresponding to a first test-specific sequence of the plurality of test-specific sequences.

16. The mobile electronic device of claim 15, wherein the processor is further configured to match color information by matching color information corresponding to a second test pad of the plurality of test pads to color information corresponding to a second test-specific sequence of the plurality of test-specific sequences.

17. The mobile electronic device of claim 10, wherein the processor is further configured to match color information by matching color information from the first image data to corresponding color information from the second image data by performing Lab color space analysis on the color information from the first and second image data.

18. The mobile electronic device of claim 10, further comprises a display screen, and wherein the processor is configured to execute the diagnostic client to display the test results on the display.

19. A computer program product, comprising:
- a processor executable non-transitory storage medium having processor executable code embodied therein to perform color-based reaction testing of biological materials, the processor executable storage medium having:
  - processor executable program code to capture digital image information of an exposed test strip and a reference color chart in an uncalibrated environment, wherein the exposed test strip comprises a plurality of test pads, and wherein further the reference color chart comprises a plurality of color blocks arranged in a plurality of test-specific sequences,
  - processor executable program code to locate first image data within the digital image information corresponding to each of the plurality of test pads, said first image data having color information,
  - processor executable program code to locate second image data within the digital image information corresponding to each of the plurality of color blocks on the reference color chart, said second image data having color information,
  - processor executable program code to match color information from the first image data to corresponding color information from the second image data, and
  - processor executable program code to generate test results based on said matching.

20. The computer program product of claim 19, wherein the processor executable program code to capture the digital image information comprises processor executable program code to capture both the exposed test strip and the reference color chart as a single digital image in the uncalibrated environment.

* * * * *